(12) United States Patent
An et al.

(10) Patent No.: US 11,612,359 B2
(45) Date of Patent: Mar. 28, 2023

(54) RENAL DYSFUNCTION RISK STRATIFICATION

(71) Applicant: Cardiac Pacemakers, Inc., St. Paul, MN (US)

(72) Inventors: Qi An, Blaine, MN (US); Yi Zhang, Plymouth, MN (US); Viktoria A. Averina, Shoreview, MN (US); Jeffrey E. Stahmann, Ramsey, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 646 days.

(21) Appl. No.: 15/478,433

(22) Filed: Apr. 4, 2017

(65) Prior Publication Data

US 2017/0290551 A1    Oct. 12, 2017

Related U.S. Application Data

(60) Provisional application No. 62/319,052, filed on Apr. 6, 2016.

(51) Int. Cl.
| | |
|---|---|
| *A61B 5/00* | (2006.01) |
| *A61B 5/053* | (2021.01) |
| *A61B 5/08* | (2006.01) |
| *A61B 5/11* | (2006.01) |
| *A61B 7/00* | (2006.01) |
| *A61B 5/20* | (2006.01) |

(Continued)

(52) U.S. Cl.
CPC .......... *A61B 5/7275* (2013.01); *A61B 5/053* (2013.01); *A61B 5/08* (2013.01); *A61B 5/1118* (2013.01); *A61B 5/201* (2013.01); *A61B 5/686* (2013.01); *A61B 7/00* (2013.01); *A61B 7/006* (2013.01); *G16H 40/63* (2018.01); *G16H 50/20* (2018.01); *G16H 50/30* (2018.01)

(58) Field of Classification Search
CPC ........ A61B 5/7275; A61B 5/053; A61B 5/08; A61B 5/1118; A61B 5/201; A61B 5/686; A61B 7/00; A61B 7/006; G16H 50/30
See application file for complete search history.

(56) References Cited

U.S. PATENT DOCUMENTS

| | | |
|---|---|---|
| 6,695,790 B2 | 2/2004 | Van Oort et al. |
| 7,529,580 B2 | 5/2009 | Gill et al. |

(Continued)

*Primary Examiner* — Lynsey C Eiseman
*Assistant Examiner* — Jessandra F Hough
(74) *Attorney, Agent, or Firm* — Schwegman Lundberg & Woessner, P.A.

(57) ABSTRACT

Systems and methods for assessing a patient's risk of renal dysfunction are described. A system may include sensor circuits to sense physiological signals and processors to generate signal metrics from the physiological signals. The system may generate a primary renal risk indication using a first signal metric, and a secondary renal risk indication using at least a second signal metric. The system may generate a composite renal risk indication and estimate a glomerular filtration rate or a chronic kidney disease stage using at least the primary and secondary risk indications. The composite renal risk indication, which indicative of a degree of renal dysfunction, may be presented to a clinician, or provided to a detector for detecting worsening heart failure.

19 Claims, 4 Drawing Sheets

(51) Int. Cl.
*G16H 50/30* (2018.01)
*G16H 50/20* (2018.01)
*G16H 40/63* (2018.01)

(56) References Cited

U.S. PATENT DOCUMENTS

| | | |
|---|---|---|
| 8,246,563 B2 | 8/2012 | Wariar |
| 8,346,356 B2 | 1/2013 | Girouard et al. |
| 2006/0010090 A1* | 1/2006 | Brockway ............ A61B 5/0002 706/46 |
| 2008/0119750 A1* | 5/2008 | Patangay ............... A61B 5/025 600/528 |
| 2008/0119907 A1* | 5/2008 | Stahmann .............. A61B 5/417 607/40 |
| 2012/0303079 A1* | 11/2012 | Mahajan ............ A61N 1/36557 607/14 |
| 2013/0236981 A1* | 9/2013 | Haick .................... G01N 27/26 436/149 |
| 2015/0355196 A1* | 12/2015 | Anderberg ............. G16B 40/00 435/7.92 |
| 2016/0354032 A1* | 12/2016 | Wariar ................ A61M 5/1723 |
| 2017/0228506 A1* | 8/2017 | Nadkarni ............... A61B 5/201 |

* cited by examiner

RENAL DYSFUNCTION RISK STRATIFICATION

CLAIM OF PRIORITY

This application claims the benefit of priority under 35 U.S.C. § 119(e) of U.S. Provisional Patent Application Ser. No. 62/319,052, filed on Apr. 6, 2016, which is herein incorporated by reference in its entirety.

TECHNICAL FIELD

This document relates generally to medical devices, and more particularly, to systems, devices and methods for detecting renal dysfunction.

BACKGROUND

Congestive heart failure (CHF or HF) is a major health problem and affects many people around the world. CHF patients may have enlarged heart with weakened cardiac muscles, resulting in poor cardiac output of blood. Although CHF is usually a chronic condition, it may occur suddenly. It may affect the left heart, right heart or both sides of the heart. If CHF affects the left ventricle, signals that control the left ventricular contraction are delayed, and the left and right ventricles do not contract simultaneously. Non-simultaneous contractions of the left and right ventricles further decrease the pumping efficiency of the heart.

The cardiovascular system maintains an interaction with other organs and systems of the body. For example, there is an identified association between cardiovascular diseases in patients with end-stage renal disease. Chronic kidney disease (CKD) is a worldwide public health problem with a rising incidence and a prevalence associated with poor outcomes and high cost. CKD may result from diseases that cause gradual destruction of the kidneys from mild dysfunction to severe kidney failure, and progression may continue to end-stage renal disease. Chronic renal failure usually occurs over a number of years as the internal structures of the kidney are slowly destroyed. Many CHF patients may have concomitant renal dysfunction, such as chronic renal insufficiency. Worsening renal function in the absence of primary renal disease is also a major determinant of worsened outcomes in HF. Additionally, hospitalized CHF patients who have worsening renal function may also carry a significantly poorer prognosis.

SUMMARY

Patients with chronic kidney disease (CKD) may be at elevated risk for subsequent cardiovascular events such as worsening heart failure. The renal risk stratification, such as identifying those patients who are at high risk of worsening renal function, or to predict the severity of the renal dysfunction, may provide diagnostic information about heart failure progression, or be used to titrate heart failure therapies.

Systems, devices and methods described herein, among other things, may be used for renal risk stratification. A system includes sensor circuits to sense physiological signals and processors to generate signal metrics from the physiological signals. The system generates a primary renal risk indication using a first signal metric, and a secondary renal risk indication using at least a second signal metric. The system may generate a composite renal risk indication and estimate a glomerular filtration rate or a chronic kidney disease stage using at least the primary and secondary risk indications. The composite renal risk indication, which indicative of a degree of renal dysfunction, may be presented to a clinician, or provided to a detector for detecting worsening heart failure.

In Example 1, a system for identifying a patient's risk of renal dysfunction is disclosed. The system may comprise sensor circuits including sense amplifier circuits to sense at least first and second physiological signals, a signal processor circuit configured to generate a first signal metric from the first physiological signal and a second signal metric from the second physiological signal. The system may include a risk stratifier circuit coupled to the signal processor circuit and configured to generate a primary renal risk indication using at least the first signal metric and generate a secondary renal risk indication using at least the second signal metric, and to generate a composite renal risk indication indicative of a degree of renal dysfunction using both the primary and secondary renal risk indications.

Example 2 may include, or may optionally be combined with the subject matter of Example 1 to optionally include, an implantable device that includes one or more of the sensor circuits, the signal processor circuit, or the risk stratifier circuit.

Example 3 may include, or may optionally be combined with the subject matter of one or any combination of Examples 1 or 2 to include, the risk stratifier circuit that may be configured to generate one or more of an estimated glomerular filtration rate (eGFR), a first probability of the eGFR falling within a GFR range, an estimated chronic kidney disease (eCKD) stage, or a second probability of the eCKD falling within a CKD stage range.

Example 4 may include, or may optionally be combined with the subject matter of Example 3 to optionally include, an output circuit that may generate an alert in response to the eGFR, the eCKD stage, or the first or second probability satisfying a respective condition.

Example 5 may include, or may optionally be combined with the subject matter of one or any combination of Examples 1 through 4 to include, the output circuit that may provide the composite renal risk indication to a cardiac event detector circuit configured to detect a worsening heart failure event.

Example 6 may include, or may optionally be combined with the subject matter of Example 5 to optionally include, the cardiac event detector that may be configured to detect the worsening heart failure event operated under an operating mode based on at least the composite renal risk indication.

Example 7 may include, or may optionally be combined with the subject matter of one or any combination of Examples 1 through 6 to include, the primary renal risk indication including a central tendency of a plurality of measurements of the first signal metric, and the secondary renal risk indication including a variability of the sampled measurements of the second signal metric.

Example 8 may include, or may optionally be combined with the subject matter of one or any combination of Examples 1 through 7 to include, the risk stratifier circuit that may be configured to generate the composite renal risk indication using a linear or a nonlinear combination of the primary and secondary renal risk indications.

Example 9 may include, or may optionally be combined with the subject matter of one or any combination of Examples 1 through 8 to include, the first physiological signal including a heart sound signal. The first signal metric may include one of an intensity measure of a first heart sound (S1), a second heart sound (S2), a third heart sound (S3), or a fourth heart sound (S4), a ratio of a S3 intensity to a reference heart sound intensity, the reference heart sound intensity including one of a S1 intensity, a S2 intensity, or a heart sound energy during a specified portion of a cardiac cycle, or a pre-ejection period, including a time interval between a Q wave and a S1 heart sound within a cardiac cycle.

Example 10 may include, or may optionally be combined with the subject matter of one or any combination of Examples 1 through 9 to include, the second physiological signal including a respiration signal. The second signal metric may include one of a respiration rate, a tidal volume, or a ratio of a respiration rate and a tidal volume.

Example 11 may include, or may optionally be combined with the subject matter of one or any combination of Examples 1 through 10 to include, the second sensor physiological signal including a thoracic impedance signal from the patient. The second signal metric may include thoracic impedance intensity.

Example 12 may include, or may optionally be combined with the subject matter of one or any combination of Examples 1 through 11 to include, the sense amplifier circuits that may be configured to sense a third physiological signal. The signal processor circuit may be configured to generate a third signal metric from the third physiological signal, and the risk stratifier circuit may be configured to generate the secondary renal risk indication using at least the second and third signal metrics.

Example 13 may include, or may optionally be combined with the subject matter of Example 12 to optionally include, the risk stratifier circuit that may be configured to generate the secondary renal risk indication using a plurality of measurements of the second signal metric when the third signal metric satisfies a specified condition.

Example 14 may include, or may optionally be combined with the subject matter of one or any combination of Examples 12 or 13 to include, the third sensor physiological signal including a physical activity signal. The third signal metric may include one of a physical activity level, or a time duration when the physical activity level meets a specified condition.

Example 15 may include, or may optionally be combined with the subject matter of one or any combination of Examples 1 through 14 to include, the risk stratifier circuit that may be configured to adjust the composite renal risk indication using clinical information about the patient. The clinical information may include one or more of a historical renal decompensation event, one or more comorbidities of CKD, a creatinine blood test, patient physical assessment, or patient demographics.

In Example 16, a method for identifying a patient's risk of renal dysfunction using a medical system is disclosed. The method may include steps of: sensing, via the medical system, at least first and second physiological signals; processing, via the medical system, the first physiological signal to generate a first signal metric and processing the second physiological signal to generate a second signal metric; estimating a risk of renal dysfunction via the medical system; and providing the composite renal risk indication to a user or a process. The estimation of the risk of renal dysfunction may include generating a primary renal risk indication using at least the first signal metric and generating a secondary renal risk indication using at least the second signal metric, and generating a composite renal risk indication using the primary and secondary renal risk indications.

Example 17 may include, or may optionally be combined with the subject matter of Example 16 to optionally include, a method of generating one or more of an estimated glomerular filtration rate (eGFR), a first probability of the eGFR falling within a GFR range, an estimated chronic kidney disease (eCKD) stage, or a second probability of the eCKD falling within a CKD stage range.

Example 18 may include, or may optionally be combined with the subject matter of Example 17 to optionally include, a method of generating an alert in response to the eGFR, the eCKD stage, or the first or second probability satisfying a respective condition.

Example 19 may include, or may optionally be combined with the subject matter of Example 16 to optionally include, a step of detecting a worsening heart failure event operated under an operating mode based on at least the composite renal risk indication.

Example 20 may include, or may optionally be combined with the subject matter of Example 16 to optionally include, a method of sensing a third physiological signals and processing the third physiological signal to generate a third signal metric. The secondary renal risk indication may be generated using at least the second and third signal metrics.

Example 21 may include, or may optionally be combined with the subject matter of Example 20 to optionally include, the method of generating the secondary renal risk indication which may include sampling a plurality of measurements of the second signal metric when the third signal metric satisfies a specified condition, and generating the secondary renal risk indication using the sampled measurements of the second signal metric.

Example 22 may include, or may optionally be combined with the subject matter of Example 20 to optionally include, the first signal metric that may be generated from a heart sound signal, the second signal metric that may be generated from a respiration signal or a thoracic impedance signal, and the third signal metric that may be generated from a physical activity signal.

Example 23 may include, or may optionally be combined with the subject matter of Example 16 to optionally include, the method of generating a composite renal risk indication that may include adjusting renal risk based on clinical information about the patient. The clinical information may include one or more of a historical renal decompensation event, one or more comorbidities of CKD, a creatinine blood test, patient physical assessment, or patient demographics.

The systems, devices, and methods discussed in this document may improve the medical technology of automated monitoring of patients with chronic kidney disease (CKD). Estimation of glomerular filtration rate or a CKD stage based on primary and secondary risk indications from different sensor signals may enhance the performance and functionality of a medical system or an ambulatory medical device for CKD patient management. In certain examples, the enhanced device functionality may include more timely detection of CKD with increased accuracy at little to no additional cost. The improvement in system performance and functionality, provided by the present systems and methods, can reduce healthcare costs associated with management and hospitalization of CKD patients. The systems, devices, and methods discussed in this document also allow for more efficient device memory usage, such as by storing sensor signal metrics that are clinically more relevant to worsening CKD. As fewer false positive detections are provided, device battery life can be extended, fewer unnecessary drugs and procedures may be scheduled, prescribed, or provided, and an overall system cost savings may be realized.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for assessing risk of worsening renal function in a patient using multiple physiological sensors. The risk assessment may be presented to a clinician or to a process such as for detecting progression of cardiac diseases such as worsening heart failure (WHF) events. The systems, devices, and methods described herein may be used in the context of diagnostics of HF comorbidities and worsening chronic diseases such as pulmonary congestion, pneumonia, or renal diseases, or to stratify patient risks of developing other dysfunctions such as cardio-pulmonary system dysfunctions.

Figure 1:
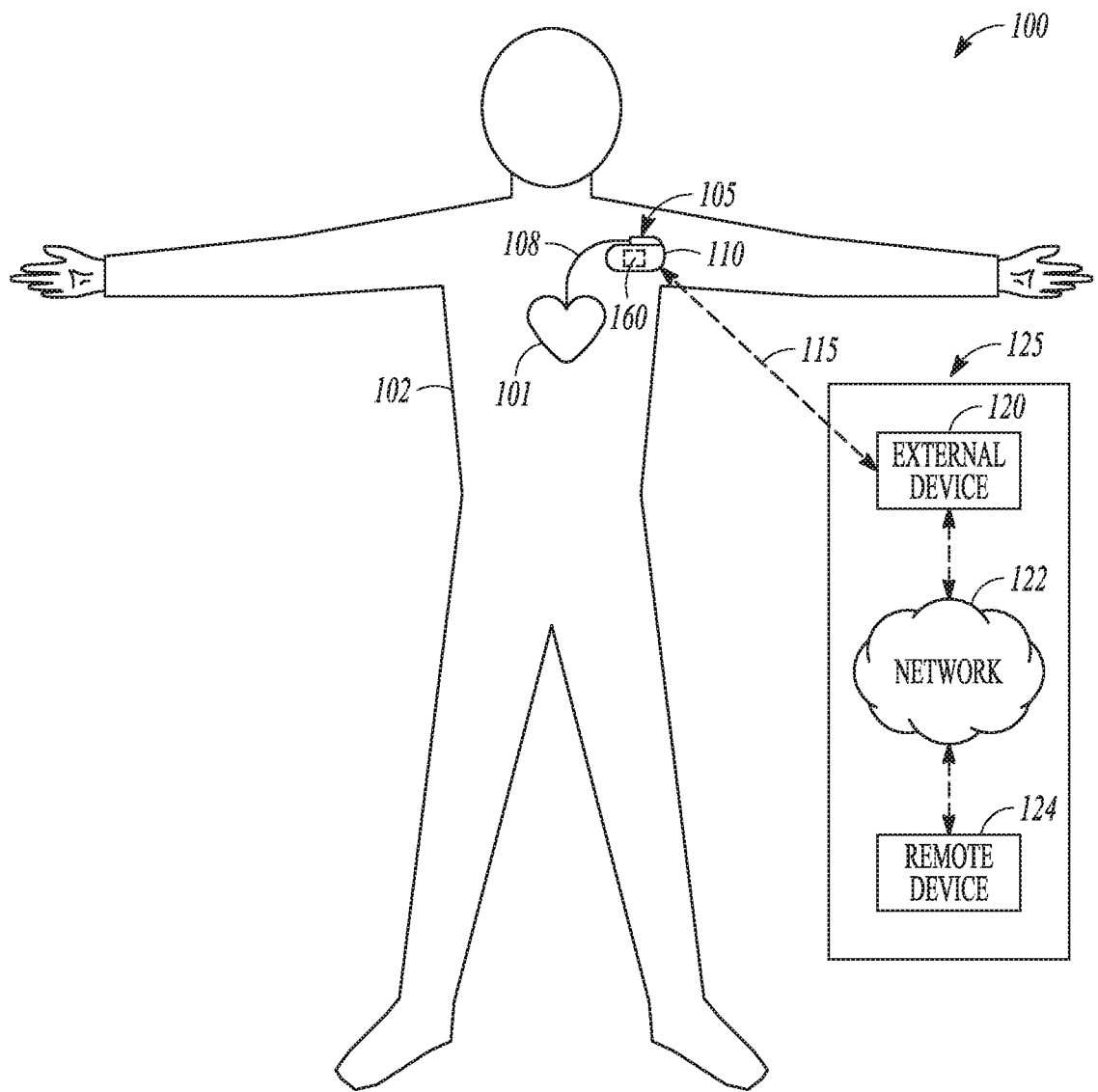
FIG. 1 illustrates generally an example of a patient management system and portions of an environment in which the patient management system may operate.

FIG. 1 illustrates generally an example of a patient management system 100 and portions of an environment in which the patient management system 100 may operate. The patient management system 100 may include an ambulatory system 105 associated with a patient body 102, an external system 125, and a telemetry link 115 providing for communication between the ambulatory system 105 and the external system 125.

The ambulatory system 105 may include an ambulatory medical device (AMD) 110 and a therapy delivery system such as a lead system 108. The AMD 110 may include an implantable device that may be implanted within the body 102 and coupled to a heart 101 via the lead system 108. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices, or patient monitors, among others. The AMD 110 may alternatively or additionally include subcutaneously implanted devices such as a subcutaneous ICD or a subcutaneous diagnostic device, wearable medical devices such as patch based sensing device, or other external monitoring or therapeutic medical devices such as a bedside monitor. In some examples, the ambulatory system 105 may include one or more implantable medical devices, or one or more wearable or holdable devices. The ambulatory system 105 may include a combination of one or more implantable medical devices, one or more wearable devices or one or more holdable devices.

The lead system 108 may include one or more transvenously, subcutaneously, or non-invasively placed leads or catheters. Each lead or catheter may include one or more electrodes for delivering pacing, cardioversion, defibrillation, neuromodulation, drug therapies, or biological therapies, among other types of therapies. In an example, the electrodes on the lead system 108 may be positioned inside or on a surface of at least a portion of the heart, such as a right atrium (RA), a right ventricle (RV), a left atrium (LA), a left ventricle (LV), or any tissue between or near the heart portions. The arrangements and uses of the lead system 108 and the associated electrodes may be determined based on the patient need and the capability of the AMD 110.

The AMD 110 may house an electronic circuit for sensing a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiological response to activity, posture, respiration, body weight, body chemical, or body temperature. The AMD 110 may initiate or adjust therapies based on the sensed physiological signals.

The patient management system 100 may include a renal dysfunction detector circuit 160 provided for patient management using at least diagnostic data acquired by the ambulatory system 105. The renal dysfunction detector circuit 160 may analyze the diagnostic data for patient monitoring, risk stratification, and detection of events such as WHF, or one or more HF comorbidities. In an example as illustrated in FIG. 1, the renal dysfunction detector circuit 160 may be substantially included in the AMD 110. Alternatively, the renal dysfunction detector circuit 160 may be substantially included in the external system 125, or be distributed between the ambulatory system 105 and the external system 125.

The external system 125 may be used to program the AMD 110. The external system 125 may include a programmer, or a patient management system that may access the ambulatory system 105 from a remote location and monitor patient status and/or adjust therapies. By way of example and not limitation, and as illustrated in FIG. 1, the external system 125 may include an external device 120 in proximity of the AMD 110, a remote device 124 in a location relatively distant from the AMD 110, and a telecommunication network 122 linking the external device 120 and the remote device 124. The telemetry link 115 may be an inductive telemetry link, or a radio-frequency (RF) telemetry link. The telemetry link 115 may provide for data transmission from the AMD 110 to the external system 125. This may include, for example, transmitting real-time physiological data acquired by the AMD 110, extracting physiological data acquired by and stored in the AMD 110, extracting patient history data such as data indicative of occurrences of arrhythmias, occurrences of decompensation, and therapy deliveries recorded in the AMD 110, and extracting data indicating an operational status of the AMD 110 (e.g., battery status and lead impedance). The telemetry link 115 may also provide for data transmission from the external system 125 to the AMD 110. This may include, for example, programming the AMD 110 to perform one or more of acquiring physiological data, performing at least one self-diagnostic test (such as for a device operational status), delivering at least one therapy, or analyzing data associated with patient health conditions such as progression of heart failure.

Portions of the AMD 110 or the external system 125 may be implemented using hardware, software, or any combination of hardware and software. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
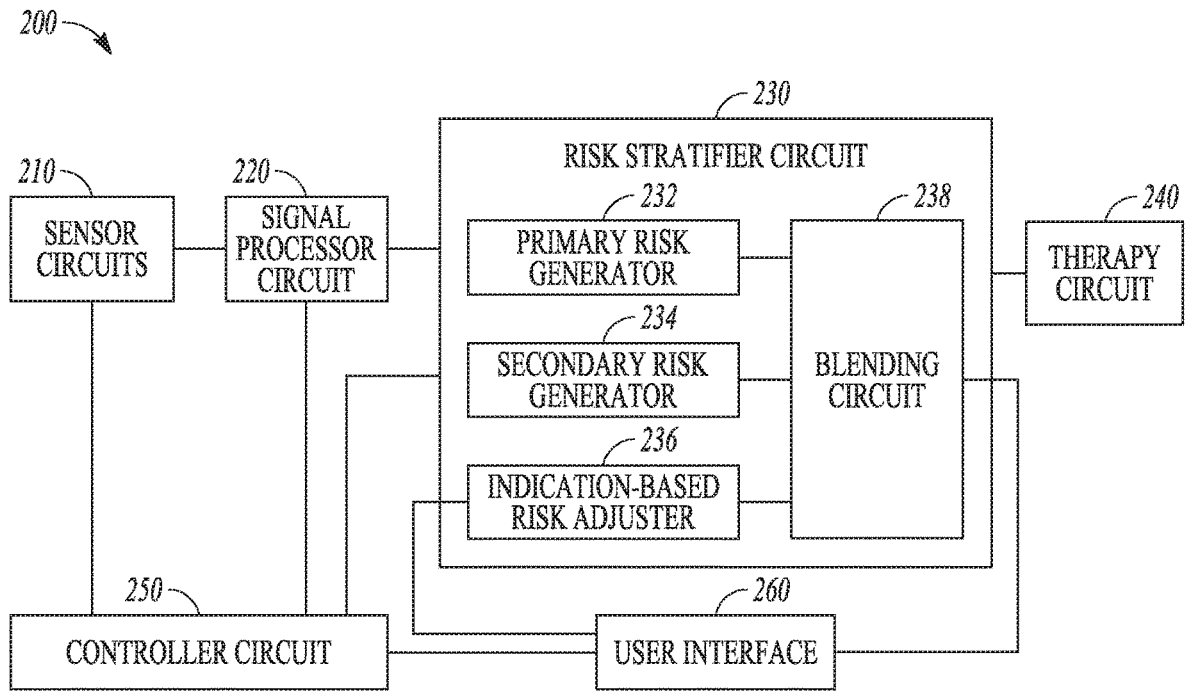
FIG. 2 illustrates generally an example of a renal dysfunction risk stratification system for identifying patient risk of worsening renal function.

FIG. 2 illustrates generally an example of a renal dysfunction risk stratification system 200 for identifying patient risk of worsening renal function, such as chronic or acute kidney failure. The renal dysfunction risk stratification system 200 may continuously or periodically (such as at specified time intervals or upon a triggering event) monitor a patient's renal function, and present the detected renal risks to a person or a data storage unit, or provide the renal risks to a process such as for detecting worsening cardiac status. A portion of the renal dysfunction risk stratification system 200 may be implemented within the AMD 110, distributed between two or more implantable or wearable medical devices (such as an implantable medical device and a subcutaneous medical device), or distributed between the AMD 110 and the external system 125.

The renal dysfunction risk stratification system 200 may include one or more of sensor circuits 210, a signal processor circuit 220, a risk stratifier circuit 230, a controller circuit 250, and a user interface 260. The sensor circuits 210 may include a plurality of sense amplifiers to sense physiological signals received from a subject. By way of non-limiting examples, the sensor circuits 210 may include a first sense amplifier circuit to sense a first physiological signal and a second sense amplifier circuit to sense a second physiological signal. In an example, a third sense amplifier circuit may be included to sense a third physiological signal. The sensed physiological signals may represent intrinsic physiological activities, evoked physiological activities when the heart or other tissues are stimulated, or physiological activities under other specified conditions. The sense amplifiers may be coupled to one or more electrodes such as on the lead system 108, or one or more implantable, wearable, or other ambulatory physiological sensors, to sense the respective physiological signal(s). Examples of physiological sensors may include pressure sensors, flow sensors, impedance sensors, accelerometers, microphone sensors, respiration sensors, temperature sensors, or blood chemical sensors, among others. Examples of the physiological signals sensed by the sensor circuits 210 may include electrocardiograph (ECG), an electrogram (EGM), an intrathoracic impedance signal, an intracardiac impedance signal, an arterial pressure signal, a pulmonary artery pressure signal, a RV pressure signal, a LV coronary pressure signal, a coronary blood temperature signal, a blood oxygen saturation signal, central venous pH value, a heart sound (HS) signal, an intracardiac or endocardial acceleration signal, a posture signal, a physical activity signal, a biomarker signal, or a respiration signal, among others. In some examples, one or more of the sense amplifiers may retrieve the respective physiological signals stored in a storage device such as an external programmer, an electronic medical record (EMR) system, or a memory unit, among other storage devices.

The signal processor circuit 220, coupled to the physiological sensor circuit 210, may include filters for filtering the physiological signals and generate respective signal metrics. By way of non-limiting examples, the signal processor circuit 220 may include a first filter circuit to filter the first sensed physiological signal to produce a trend of a first signal metric X1, and a second filter circuit to filter the second sensed physiological signal to produce a trend of a second signal metric X2. In an example, a third filter circuit may be included to filter the third sensed physiological signal to produce a trend of a third signal metric X3. The signal metrics may include statistical parameters extracted from the sensed physiological signal, such as signal mean, median, or other central tendency measures or a histogram of the signal intensity, among others. Additionally or alternatively, the signal metrics may include morphological parameters such as maximum or minimum within a specified time period such as a cardiac cycle, positive or negative slope or higher order statistics, or signal power spectral density at a specified frequency range, among other morphological parameters.

The signal metrics may be generated from different physiological signals sensed by different physiological sensors. In some examples, two or more of the signal metrics X1, X2, and X3 may be generated from the same physiological signal. The filters may have different filter characteristics, such as filter coefficients associated with cutoff frequencies or gains within a frequency band, or temporal segment of the physiological signal from which the signal metrics are generated. Depending on the physiological signal, various first and second signal metrics may be generated. In an example, a thoracic or cardiac impedance signal may be sensed using the electrodes on the lead system 108, and impedance metrics may include thoracic impedance magnitude within a specified frequency range obtained from. In an example, a heart sound (HS) signal may be sensed from an accelerometer, a microphone, or an acoustic sensor coupled to the AMD 110, and HS metrics may include intensities of first (S1), second (S2), third (S3), or fourth (S4) heart sound components or a relative intensity such as a ratio between two heart sound components, timing of one of the S1, S2, S3, or S4 heart sound components relative to a fiducial point such as a P wave, Q wave, or R wave in an ECG. In an example, a respiration signal may be sensed using an impedance sensor or an accelerometer, and the respiratory metric may include a respiratory rate, a tidal volume, or a rapid-shallow breathing index (RSBI) computed as a ratio of a respiratory rate measurement to a tidal volume measurement. In another example, a physical activity signal may be sensed using an accelerometer, and the activity metrics may include physical activity intensity, or a time duration when the activity intensity is within a specified range or above a specified threshold. In yet another example, a blood pressure signal may be sensed using a pressure sensor, and the pressure metrics may include systolic blood pressure, diastolic blood pressure, mean arterial pressure, and the timing metrics of these pressure measurements with respect to a fiducial point.

A signal metric trend may be formed using multiple measurements of the signal metric during a specified time period. In an example, the signal metric trend may include a daily trend including daily measurement of a signal metric over a specified number of days. Each daily measurement may be determined as a central tendency of a plurality of measurements obtained within a day. In an example, a thoracic impedance trend may be generated using portions of the received impedance signal during identical phases of a cardiac cycle such as within a certain time window relative to R-wave in a ECG signal), or at identical phases of a respiratory cycle such as within an inspiration phase or an expiration phase of a respiration signal. This may minimize or attenuate the interferences such as due to cardiac or respiratory activities, in the impedance measurements. In another example, a thoracic impedance trend may be generated using portions of the received impedance signal during a specific type of posture or during a specific level of physical activity intensity, such as when the patient is lying down or undergoing light, mild or moderate physical activity. This may attenuate the interferences due to variation in postures or activity intensity in the impedance measurements. The thoracic impedance trend may be generated using impedance measurements collected during one or more impedance acquisition and analysis sessions. In an example, an impedance acquisition and analysis session may start between approximately 5 a.m. and 9 a.m. in the morning, and lasts for approximately 2-8 hours. In another example, the impedance acquisition and analysis session may be programmed to exclude certain time periods, such as night time, or when the patient is asleep. The impedance parameter may be determined as a median of multiple impedance measurements acquired during the impedance acquisition and analysis session.

The risk stratifier circuit 230 may be coupled to the signal processor circuit 220 to produce a risk indication indicative of a degree of renal dysfunction. The risk indication may have categorical values indicating risk degrees such as "high", "medium", or "low" risks, or alternatively numerical risk scores within a specified range. The risk scores may have discrete values (e.g., integers from 0 through 5) or continuous values (e.g., real numbers between 0 and 1), where a larger risk score indicates a higher risk.

The risk stratifier circuit 230 may be implemented as a part of a microprocessor circuit. The microprocessor circuit may be a dedicated processor such as a digital signal processor, application specific integrated circuit (ASIC), microprocessor, or other type of processor for processing information including the physiological signals received from the sensor circuits 210. Alternatively, the microprocessor circuit may be a general purpose processor that may receive and execute a set of instructions of performing the functions, methods, or techniques described herein.

The risk stratifier circuit 230 may include circuit sets comprising one or more other circuits or sub-circuits, such as a primary risk generator 232, a secondary risk generator circuit 234, an optional indication-based risk adjuster 236, and a blending circuit 238, as illustrated in FIG. 2. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The primary risk generator 232 may receive from the signal processor circuit 220 a plurality of measurements of the first signal metric (X1), and generate a primary renal risk indication (R1) using at least X1. The primary renal risk indication may include a statistical measure, such as a central tendency, a variability, or other first, second, or higher order statistics, of the plurality of the measurements of the signal metric X1. Examples of the first signal metric may include heart sound signal metrics such as S1 intensity, S2 intensity, S3 intensity, S4 intensity, or a ratio of a S3 intensity to a reference heart sound intensity (which may include a S1 intensity, S2 intensity, or heart sound energy during a specified portion of the cardiac cycle). In another example, the first signal metric may include an estimated pre-ejection period (PEP) such as a time interval between a Q wave on an ECG and a S1 heart sound within a cardiac cycle.

The secondary risk generator 234 may receive from the signal processor circuit a plurality of measurements of the second signal metric X2, and to generate a secondary renal risk indication (R2) using at least the measurements of X2. Examples of the second signal metric X2 may include a respiration signal metric, such as a respiratory rate, a tidal volume, or a rapid-shallow breathing index (RSBI) computed as a ratio of the respiratory rate to the tidal volume. A patient who breathes rapidly (high respiratory rate) and shallowly (low tidal volume) tends to have a high RSBI. Other examples of X2 may include thoracic impedance magnitude indicating thoracic fluid accumulation.

In some examples, the secondary risk generator 234 may generate the secondary renal risk indication (R2) using a plurality of measurements of X2 and a plurality of measurements of X3. Examples of X3 may include physical activity intensity, or a time duration when the physical activity intensity satisfies a specified condition such as above a threshold. The secondary renal risk indication (R2) may be generated using a weighted linear or nonlinear combination of the second and third signal metrics X2 and X3. In an example, the secondary renal risk indication (R2) may be computed as the second signal metric X2 weighted by the third signal metric X3. In another example, the secondary renal risk indication R2 may be determined using sampled measurements of the second signal metric X2 conditional upon the third signal metric X3 satisfying a specified condition, such as exceeding a specified threshold. In an example, the second signal metric X2 includes a respiratory rate and the third signal metric X3 includes physical activity intensity or the duration of the physical activity above a threshold. The respiratory rate measurements may be sampled during a time period when a high physical activity is indicated, such as when the physical activity intensity exceeds a specified threshold. The secondary renal risk indication (R2) may be computed as a statistical measure, such as a central tendency or a variability, of the conditionally sampled respiratory rate measurements.

The blending circuit 238 may combine the primary and secondary renal risk indications R1 and R2 to generate a composite renal risk indication (cR), such as according to a fusion model. A fusion model may include one or more signal metrics and an algorithm for computing a risk indication from the one or more signal metrics. Examples of the fusion models may include a linear weighted combination, a nonlinear combination such as a decision tree, a neural network, a fuzzy-logic model, or a multivariate regression model, among others. In an example, the primary renal risk indication R1 includes a central tendency or other first-order statistics of a plurality of measurements of the signal metric X1, and the secondary renal risk indication R2 includes a variability or other second-order statistics of a plurality of measurements of X2, or of a linearly or nonlinearly combined metric between X2 and X3, or conditionally sampled X2 measurements when X3 satisfies specified conditions. The blending circuit 238 may generate the composite renal risk indication cR by combining R1 and R2. In an example, the blending circuit 238 may include a renal function estimator for estimating a degree of renal dysfunction, as will be discussed below with reference to FIG. 4.

The optional indication-based risk adjuster 236 may adjust the renal risk indications R1 or R2 according to information about the patient clinical indications. The clinical indications may include patient medical history such as historical renal decompensation events, one or more comorbidities of CKD, creatinine blood test, urine test, heart failure comorbidities, exacerbation of recent chronic disease, a previous medical procedure, patient medication intake or other treatment undertaken, patient physical assessment, or patient demographics such as age, gender, race, or ethnicity. The clinical indications may be provided by a clinician such as via the user interface 260, or stored in a memory such as an electronic medical record (EMR) system. The blending circuit 238 may generate the composite renal risk indication further using the patient's clinical indications. In an example, the composite renal risk indication cR may be adjusted by the clinician such as via the user interface 260 according to the patient's clinical indications.

In some examples, the patient clinical indications may have time-varying effect on the patient risk of developing a future disease. For example, a more recent disease state or a surgery may put the patient at higher risk for developing a future worsening renal disease than a more remote historical disease in patient medical history. To account for the time-varying effect of the historical medical event, in an example, the indication-based risk adjuster 236 may produce time-varying weight factors decaying with time elapsed from a historical medical event, and apply the time-varying weight factors to at least one of the primary or secondary renal risk indications R1 or R2. The time-varying weight factor may follow a linear, exponential, or other nonlinear decay function of the time elapsed from a historical medical event. In another example, the blending circuit 238 may adjust at least one of R1 or R2 temporarily. For example, the indication-based risk adjuster 236 may be configured to maintain elevated risks of R1 or R2 above a baseline risk score within a specified timeframe following a historical medical event, and resume to the baseline risk score beyond the specified timeframe.

In some examples, the blending circuit 238 may generate the composite renal risk indication cR according to a fusion model selected based on signal quality of the physiological signals from which the signal metrics (such as X1, X2, or X3) are generated. For example, a fusion model that employs a physiological signal with a high signal-to-noise ratio (SNR) or less signal variability is preferred over another fusion model that employs another physiological signal with a low SNR or excessive signal variability.

The composite renal risk indication (cR) may be presented to a system user such as a clinician via the user interface 260. Additionally or alternatively, the cR may be provided to a process for detecting a worsening cardiac status or other chronic disease. Examples of worsening cardiac status detection using at least the composite renal risk indication are discussed below, such as with reference to FIG. 3.

The controller circuit 250 may control the operations of the sensor circuits 210, the signal processor circuit 220, the risk stratifier circuit 230, the user interface unit 260, and the data and instruction flow between these components. In an example, the controller circuit 250 may configure the operations of the secondary risk generator 234, such as a combination of second and third signal metrics X2 and X3 for generating the secondary renal risk indication R2.

The user interface 260 may include a user input module and an output module. In an example, at least a portion of the user interface unit 260 may be implemented in the external system 125. The user input module may be coupled to one or more user input device such as a keyboard, on-screen keyboard, mouse, trackball, touchpad, touch-screen, or other pointing or navigating devices. The input device may enables a system user (such as a clinician) to program the parameters used for sensing the physiological signals, assessing risk indications, and detecting worsening cardiac event. The output module may generate a human-perceptible presentation of the composite renal risk indication cR, such as displayed on the display. The presentation may include other diagnostic information including the physiological signals and the signals metrics, the primary and secondary renal risk indications, as well as device status such as lead impedance and integrity, battery status such as remaining lifetime of the battery, or cardiac capture threshold, among others. The information may be presented in a table, a chart, a diagram, or any other types of textual, tabular, or graphical presentation formats, for displaying to a system user. Additionally or alternatively, an alert may be generated in response to the cR satisfies a specified condition. The alert may include audio or other human-perceptible media format.

In some examples, the renal dysfunction risk stratification system 200 may additionally include a therapy circuit 240 that is configured to deliver a therapy to the patient in response to one or more of the primary or secondary renal risk indications, or the composite renal risk indication. Examples of the therapy may include electrostimulation therapy delivered to the heart, a nerve tissue, other target tissues in response to the detection of the target physiological event, or drug therapy including delivering drug to a tissue or organ. In some examples, the therapy circuit 240 may use the primary or secondary renal risk indications or the composite renal risk indication to modify an existing therapy, such as adjusting a stimulation parameter or drug dosage.

Figure 3:
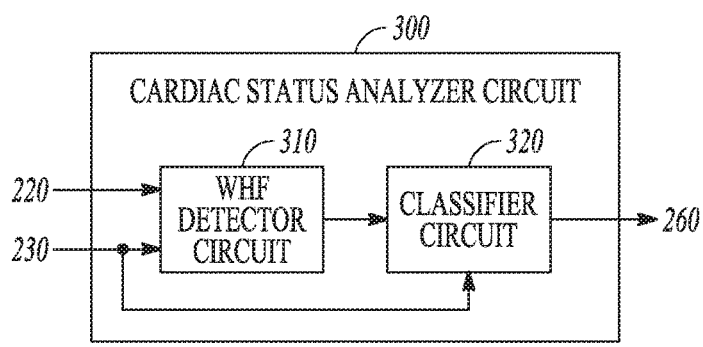
FIG. 3 illustrates generally an example of a cardiac status analyzer circuit configured to detect worsening heart failure (WHF) using the risk of renal dysfunction.

FIG. 3 illustrates generally an example of a cardiac status analyzer circuit 300 configured to detect cardiac diseases such as worsening heart failure (WHF) event using at least information about risk of renal dysfunction. The cardiac status analyzer circuit 300 may be implemented within the AMD 110, distributed between two or more implantable or wearable medical devices (such as an implantable medical device and a subcutaneous medical device), or distributed between the AMD 110 and the external system 125. In an example, the cardiac status analyzer circuit 300 may be modified and configured to detect other chronic diseases such as pulmonary diseases.

The cardiac status analyzer circuit 300 may include a WHF detector circuit 310 coupled to the risk stratifier circuit 230 to receive the composite renal risk indication (cR), and coupled to the signal processor circuit 220 to receive one or more signal metrics for detection. The signal metrics for detecting WHF may be different from the signal metrics for renal risk indication such as generated by the risk stratifier circuit 230. A temporal change a signal metric ($\Delta X_D$), such as a relative difference of the signal metric from a reference level representing a signal metric baseline, may be generated. In an example, the temporal change of a signal metric ($\Delta X_D$) may be transformed into sequence of transformed indices, such as by using a codebook that maps quantized magnitude of respective signal metric into numerical indices within a specified range, where a larger code indicates a higher signal magnitude.

The WHF detector circuit 310 may generate a detection indication using a linear or nonlinear combination of the composite renal risk indication (cR) and the $\Delta X_D$. In an example, the combination may include a logical combination, such as a decision tree. The decision tree may be implemented as a set of circuits, or a set of instructions implemented in a microprocessor circuit, such as a digital signal processor or a general purpose processor. In another example, the combination of the cR and the $\Delta X_D$ may involve a modulation of the $\Delta X_D$ by the cR. An example of the modulation may include a product of cR and the $\Delta X_D$. In another example, the modulation may include conditional sampling of the $\Delta X_D$ upon the cR satisfying a specified condition.

The WHF detector circuit 310 may be configured to detect WHF operated under an operating mode, which may include a detection algorithm for detecting WHF. In an example, the detection algorithm may be chosen based on the composite renal risk indication cR. Since patients with severe renal dysfunction may be at elevated risk of WHF, a more sensitive detection algorithm may allow timely detection of a WHF event in patients with high risk of renal dysfunction. In an example, if a high cR is indicated (e.g., cR exceeds a renal risk threshold), then the WHF detector circuit 310 may be configured to detect WHF using a detection algorithm with a high sensitivity or a low specificity to WHF event, such as an algorithm with a lower detection threshold to which the relative difference $\Delta X_D$ is compared. Conversely, if a low cR is indicated (e.g., cR does not exceed the renal risk threshold), then the WHF detector circuit 310 may be configured to detect WHF using a detection algorithm with a low sensitivity or a high specificity to WHF event, such as an algorithm with a higher detection threshold for the relative difference $\Delta X_D$.

The cardiac status analyzer circuit 300 may include a classifier circuit 320 to classify the detected WHF event as either a WHF event with concomitant CKD if the cR indicates a high probability of CKD, or a WHF event free of concomitant CKD if the cR indicates a low probability of CKD. Examples of determining the probability of CKD being within a range of stages are discussed below such as with reference to FIG. 4. The classification of WHF events may be presented to a clinician such as via the user interface 260. In an example, the detected WHF events may be ranked in an order according to the composite renal risk indications, such as a descending order of the composite renal risk indications. Compared to the WHF events with lower CKD probabilities, the WHF events with higher CKD probabilities may require closer attention from the clinician, and therefore have a higher priority to be presented to a clinician.

Figure 4:
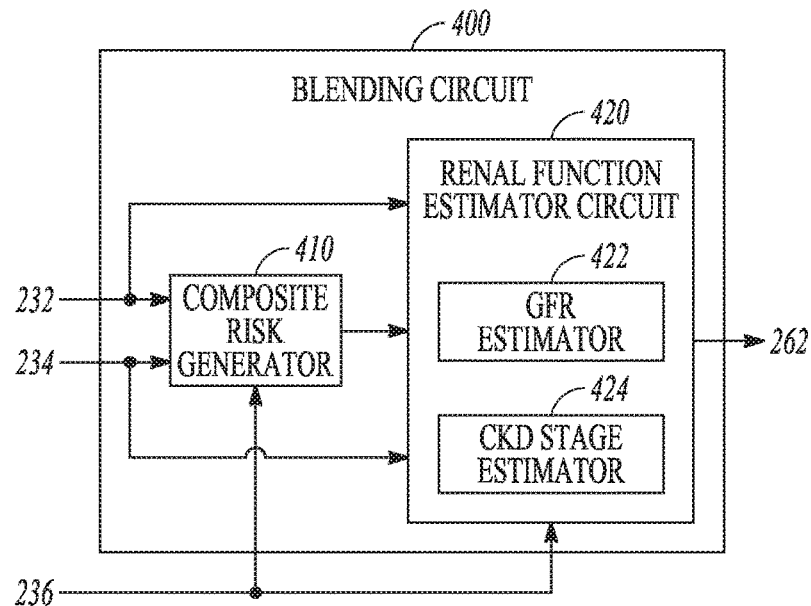
FIG. 4 illustrates generally an example of a blending circuit for generating a composite renal risk indication and estimating a degree of renal dysfunction.

FIG. 4 illustrates generally an example of a blending circuit 400 for generating a composite renal risk indication and estimating a degree of renal dysfunction. The blending circuit 400, which may be an embodiment of the blending circuit 238, may include a composite risk generator 410 and a renal function estimator circuit 420. The composite risk generator 410 may generate the composite renal risk indication cR using the primary and secondary renal risk indications R1 and R2. In an example, the composite renal risk indication cR may be computed using a logical combination of R1 and R2, such as a decision tree comprising the first and second, or first, second and third signal metrics each satisfying specified conditions such as falling within a specified range. In another example, the composite renal risk indication cR may include a numerical risk score computed as a weighted combination of risk scores associated with the first, second, and third signal metrics X1, X2 and X3. In an example, two or more signal metrics including S3 intensity, RSBI variability, PEP variability, and activity intensity may be calculated from respective signal metrics. High S3 intensity, high variability of RSBI or PEP, or physical inactivity may be indicative of an elevated risk of renal dysfunction. The composite risk generator 410 may compute a linear weighted sum of two or more of those signal metrics as the composite renal risk indication cR. The composite risk generator 410 may receive from indication-based risk adjuster 236 clinical indication and information about patient medical history, and compute the composite renal risk indication additionally using clinical indication.

The renal function estimator circuit 420 may predict worsening renal function based on the composite renal risk indication cR. The renal function estimator circuit 420 may include a glomerular filtration rate (GFR) estimator 422 to produce an estimated GFR (eGFR). In an example, the GFR estimator 422 may estimate a probability of the eGFR falling within a specified range, such as a probability that the eGFR falling below 30 milliliter per minute (mL/min), that is, P(eGFR<30). The renal function estimator circuit 420 may additionally or alternatively include a chronic kidney disease (CKD) stage estimator 424 to produce an estimated CKD (eCKD) stage. The CKD stages are clinically association with GFR levels. For example, a GFR less than 30 mL/min indicate a severe CKD (stage 4, with GFR between 15-29 mL/min) or end-stage CKD (stage 5, with GFR<15 mL/min). A GFR higher than 30 mL/min indicate a moderate CKD (stage 3A with GFR between 45-59 mL/min and stage 3B with GFR between 30-44 mL/min), a mild CKD (stage 2, with GFR between 60-89 mL/min), or normal renal function (stage 1, with GFR greater than 90 mL/min). In an example, the CKD stage estimator 424 may estimate a probability of the eCKD falling within a specified range of CKD stages, such as within stages 1-3 as denoted by P(eCKD=stages 1-3), or within stages 4-5 as denoted by P(eCKD=stages 4-5).

The GFR estimator 422 and the CKD stage estimator 424 may estimate the respective eGFR level or the eCKD stage, or the respective probabilities such as P(eGFR<30) or P(eCKD=stages 4-5), based on a comparison of the cR with one or more threshold values. Alternatively, the renal function estimator circuit 420 may predict a degree of renal dysfunction using a computational model of the primary and secondary renal risk indications R1 and R2, and optionally along with the clinical indications. In an example, the renal function estimator circuit 420 may produce a multivariate regression model of the signal metrics such as X1, X2, and X3 used for computing the composite renal risk indication cR. The multivariate regression model may additionally include clinical indication, patient medical history, or patient demographic information. Examples of the regression model may include linear, nonlinear, or logistic regression models. Other examples of the computation model may include decision trees, neural networks, or principal component analysis, among other supervised or unsupervised machine learning models.

The estimated GFR or the estimated CKD, or the probabilities of GFR or CKD falling within the specified ranges, may be presented to a system user such as a clinician. In an example, if the probability P(eGFR<30) or P(eCKD=stages 4-5) falls below a first probability threshold which indicates a substantially low likelihood of severe or end-stage CKD, then a notification may be generated, such as via the user interface 260, to indicate that further lab test of GFR level (such as a creatinine test) may not be necessary. An example of the first probability threshold is approximately 20-40%. If the probability P(eGFR<30) or P(eCKD=stages 4-5) exceeds a second probability threshold which indicates a substantially high likelihood of severe to end-stage CKD, then an alert of high GFR may be generated at the user interface 260. A recommendation may also be presented to the clinician, such as a recommendation for further creatinine test to confirm the elevated GFR level. An example of the second probability threshold is approximately 60-80%.

Figure 5:
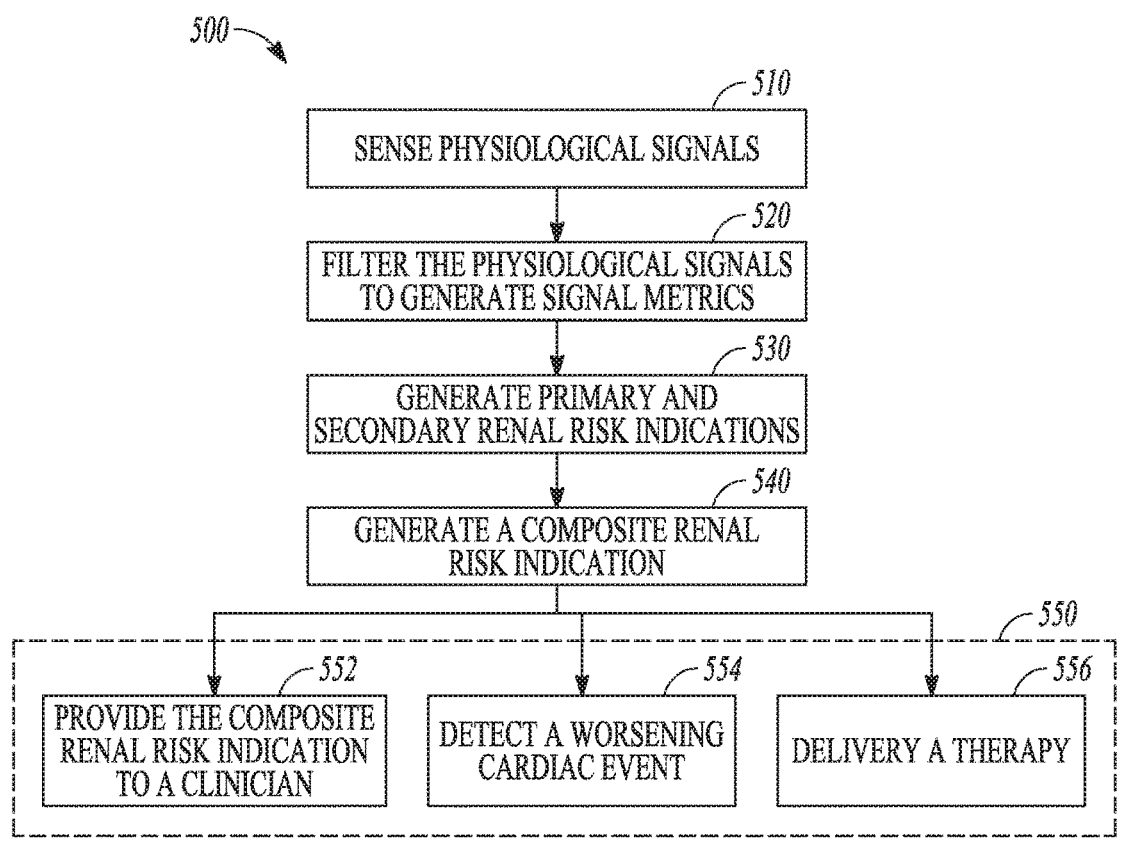
FIG. 5 illustrates generally an example of a method for identifying a patient's risk of renal dysfunction.

FIG. 5 illustrates generally an example of a method 500 for identifying a patient's risk of renal dysfunction. The renal dysfunction may be manifested as comorbid conditions in patients with chronic disease such as CHF, and may include chronic renal insufficiency or other chronic or acute kidney diseases. In an example, the method 500 may be used for screening patients and identify those who require further lab tests, such as a creatinine test, to confirm the elevated GFR level. The method 500 may be implemented in and operate by an ambulatory medical device such as an implantable or wearable medical device, or in a remote patient management system, and used to continuously or periodically monitor the patient's renal function. In an example, the method 500 may be executed by the worsening renal function detector 160 or any embodiment thereof, or by the external system 125.

The method 500 begins at 510 by sensing physiological signals from a patient. Examples of the physiological signals may include electrocardiograph (ECG), an electrogram (EGM), an intrathoracic impedance signal, an intracardiac impedance signal, an arterial pressure signal, a pulmonary artery pressure signal, a RV pressure signal, a LV coronary pressure signal, a coronary blood temperature signal, a blood oxygen saturation signal, central venous pH value, a heart sound (HS) signal, a posture signal, a physical activity signal, a respiration signal, or a body chemical, among others.

At 520, the physiological signals may be filtered to generate a plurality of signal metrics, including a first signal metric generated from a first physiological signal and a second signal metric from a second physiological signal. In some examples, a third signal metric may be generated from a third physiological signal. The signal metrics may include statistical or morphological parameters extracted from the sensed physiological signal. Examples of the signal metrics may include thoracic impedance magnitude, HS metrics such as intensities of S1, S2, S3, or S4 heart sounds or a relative intensity such as a ratio between two heart sound components, a ratio of S3 heart sound intensity to a reference heart sound intensity, timing of the S1, S2, S3, or S4 heart sound with respect to a fiducial point such as a P wave, Q wave, or R wave in an ECG, a respiratory rate, a tidal volume, a RSBI, physical activity intensity, or a time duration when the activity intensity is within a specified range or above a specified threshold, systolic blood pressure, diastolic blood pressure, mean arterial pressure, or the timing metrics of these pressure measurements with respect to a fiducial point, among others. A signal metric trend may include multiple measurements of the signal metric during a specified period of time. In an example, the signal metric trend may include a daily trend including daily measurement of a signal metric over a specified number of days.

At 530, a primary renal risk indication (R1) and a secondary renal risk indication (R2) may be generated from the signal metrics. The primary renal risk indication R1 may be determined using a statistical measure of a plurality of the measurements of the first signal metric. The statistical measure may include a central tendency, a variability, or other first or second order statistics. Examples of the first signal metric for generating the primary renal risk indication may include one of heart sound metrics including a S2 intensity, S3 intensity, a ratio of a S3 intensity to a reference heart sound intensity such as S1 intensity, S2 intensity, or heart sound energy during a specified portion of the cardiac cycle, or an estimate of pre-ejection period (PEP) such as a time interval between a Q wave on a ECG and a S1 heart sound within a cardiac cycle.

The second signal metric may include a respiration signal metric, such as a respiratory rate, a tidal volume, or a rapid-shallow breathing index (RSBI) computed as a ratio of the respiratory rate to the tidal volume, or a thoracic impedance magnitude indicating thoracic fluid accumulation. The third signal metric may include physical activity intensity, or a time duration when the physical activity intensity satisfies a specified condition such as above a threshold. In an example, the secondary renal risk indication (R2) may be based on weighted combination of the second and third signal metrics. In an example, R2 may be computed as the second signal metric weighted by the third signal metric. In another example, R2 may be determined based on conditional sampling of a signal metric. In an example, the second signal metric X2 includes a respiratory rate and the third signal metric X3 includes physical activity intensity or the duration of the physical activity above a threshold. The respiratory rate measurements may be sampled during a time period when a high physical activity is indicated, such as when the physical activity intensity exceeds a specified threshold. In an example, R1 includes a central tendency or other first-order statistics of a plurality of measurements of the first signal metric, and R2 includes a variability or other second-order statistics of a plurality of measurements of the second signal metric, or a plurality of measurements of a combination of the second and third signal metrics, or sampled measurements of the second signal metric conditional upon the third signal metric satisfying a specified condition.

At 540, a composite renal risk indication may be generated by combining at least the primary and secondary renal risk indications R1 and R2. Patient clinical indications, information about medical history, or patient demographic information may additionally be used for computing the composite renal risk indication. Examples of clinical indication, medical history information, and patient demographic information may include historical renal decompensation events, one or more comorbidities of CKD, creatinine blood test, heart failure comorbidities, exacerbation of recent chronic disease, a previous medical procedure, patient medication intake or other treatment undertaken, patient food or fluid intake, dialysis treatment, patient physical assessment, or patient demographics such as age, gender, race, or ethnicity. In some examples, to account for time-varying effect of the historical medical event on the risk of renal dysfunction, time-varying weight factors decaying with time elapsed from a historical medical event may be generated and applied to the primary or secondary renal risk indications R1 or R2. The time-varying weight factor may follow a linear, exponential, or other nonlinear decay function of the time elapsed from a historical medical event. The composite renal risk indication may be generated using a combination of R1 and R2 each weighted by the time-varying weigh factors.

Combination of R1 and R2 may be based on a fusion model. Examples of the fusion models may include a linear weighted combination, a nonlinear combination such as a decision tree, a neural network, a fuzzy-logic model, or a multivariate regression model, among others. In an example, the fusion model may be selected based on the signal quality of the one or more physiological signals from which the signal metrics are generated. For example, a fusion model that employs a physiological signal with a high signal-to-noise ratio (SNR) or less signal variability is preferred over another fusion model that employs another physiological signal with a low SNR or excessive signal variability.

At 550, the composite renal risk indication (cR) may be provided to a system user or a process. In an example, at 552 the cR may be presented to a clinician, such as being displayed on the display screen included in the user interface 260. Other diagnostic information including the physiological signals and the signals metrics, the primary and secondary renal risk indications, as well as device status may also be presented to the clinician along with the cR. The information may be presented in a table, a chart, a diagram, or any other types of textual, tabular, or graphical presentation formats.

The cR may be provided to a process for detecting a worsening cardiac event, such as a WHF event, at 554. The detection method may be implemented in and executed by the cardiac status analyzer circuit 300, as illustrated in FIG. 3. Detection of the WHF event may be based on a logical combination (such as a decision tree) of temporal change of one or more signal metrics, such as a relative difference of the signal metric from a reference level representing a signal metric baseline, and the composite renal risk indication (cR). In an example, a detection algorithm may be selected based on the composite renal risk indication cR. For example, if a high cR is indicated (e.g., cR exceeds a renal risk threshold), then a detection algorithm with a high sensitivity or a low specificity to WHF event, such as an algorithm with a lower detection threshold, is used to detected the WHF event at 554. Conversely, if a low cR is indicated (e.g., cR does not exceed the renal risk threshold), then a detection algorithm with a low sensitivity or a high specificity to WHF event, such as an algorithm with a higher detection threshold may be used to detect the WHF event at 554.

The detection of WHF event at 554 may additionally include classification of the detected WHF event as either a WHF with concomitant CKD if the cR indicates a high probability of CKD, or a WHF without concomitant CKD if the cR indicates a low probability of CKD. The classification of WHF events may be presented to a clinician. In an example, the detected WHF events may be presented in a ranked order, such as a descending order, of the composite renal risk indications.

In some examples, the cR may be provided to a process at 556 for delivering a therapy to the patient. Examples of the therapy may include electrostimulation therapy delivered to the heart, a nerve tissue, other target tissues in response to the detection of the target physiological event, or drug therapy including delivering drug to a tissue or organ. In some examples, an existing therapy may be modified at 556, such as adjusting a stimulation parameter or drug dosage.

Figure 6:
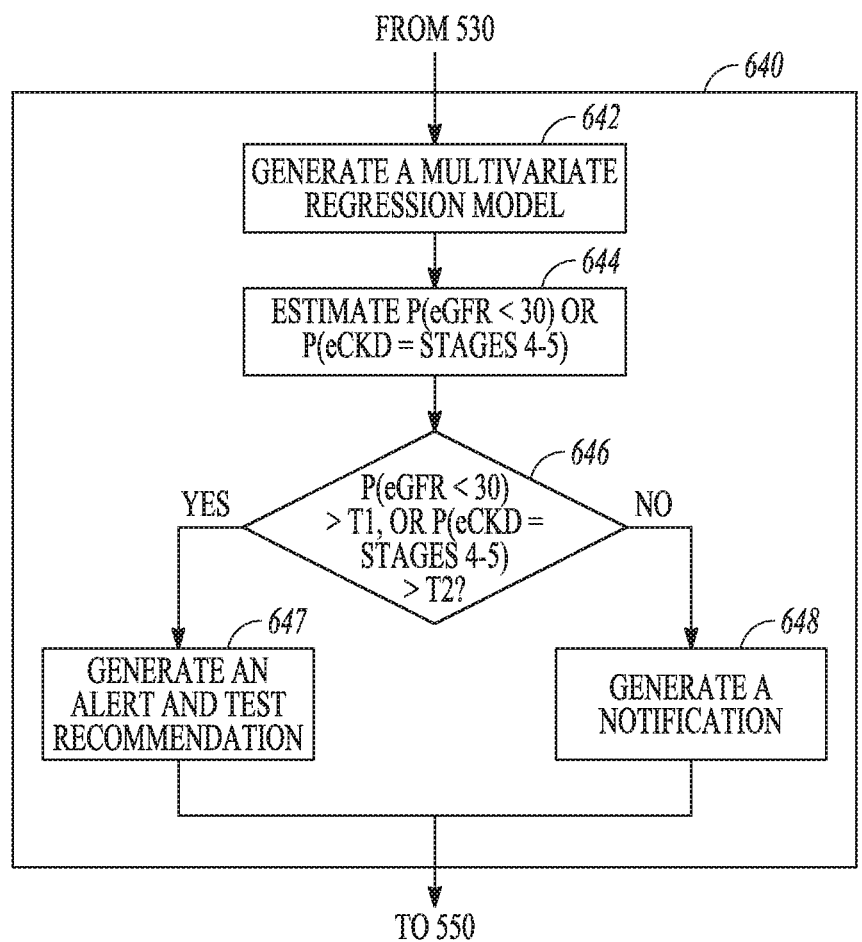
FIG. 6 illustrates generally an example of a portion of a method for estimating glomerular filtration rate level or chronic kidney disease stages.

FIG. 6 illustrates generally an example of a portion of a method 640 for estimating GFR level or CKD stages. The method 640 may be an embodiment of the composite renal risk indications at 540 as illustrated in FIG. 5. The estimation of the renal dysfunction may be based on a computational model of the primary and secondary renal risk indications R1 and R2, and optionally along with the clinical indication and information about patient medical history. In an example, the method 640 may be implemented in and executed by the renal function estimator circuit 420.

The method 640 begins at 642 by generating a multivariate regression model that includes the signal metrics such as the first (X1), second (X2), and third (X3) signal metrics used for computing the composite renal risk indication cR. Examples of the regression model may include linear, non-linear, or logistic regression models. The multivariate regression model may additionally include clinical indication, patient medical history, or patient demographic information.

At 644, low GFR or high-stage CKD may be estimated using the multivariate regression model. An estimated GFR (eGFR) or an estimated CKD (eCKD) may be used for screening patients and identify those who need creatinine test to confirm the elevated GFR level. A probability of the eGFR falling within a specified range, such as a probability that the eGFR falling below 30 milliliter per minute (mL/min), denoted by P(eGFR<30), may be generated. Additionally or alternatively, a probability of the eCKD stage falling with a specified range of stages, such as a probability that the eCKD is at stages 4 or 5, denoted by P(eCKD=stages 4-5), may be generated. Clinically, GFR less than 30 mL/min indicate a severe CKD (stage 4, with GFR between 15-29 mL/min) or end-stage CKD (stage 5, with GFR<15 mL/min).

At 646, the probabilities P(eGFR<30) or P(eCKD=stages 4-5) may be compared to respective threshold to determine worsening of renal function. If the probability P(eGFR<30) or P(eCKD=stages 4-5) exceeds the respective thresholds, it indicates a substantially high probability of severe to end-stage CKD; then at 647 an alert of high GFR may be generated and presented to the clinician such as via the user interface 260. Recommendation for further lab test to confirm the elevated GFR level, such as creatinine test, may also be presented to the clinician. However, if the probabilities P(eGFR<30) or P(eCKD=stages 4-5) are less than their respective thresholds, it indicates the patient is less likely to have a severe or end-stage CKD, then at 648 a notification, including the probabilities P(eGFR<30) or P(eCKD=stages 4-5), may be generated and presented to the clinician, with no recommendation for further lab test of GFR level. In an example, the thresholds of the probabilities P(eGFR<30) or P(eCKD=stages 4-5) for producing the alert and recommending further lab test is approximately 60-80%; and the thresholds of the probabilities P(eGFR<30) or P(eCKD=stages 4-5) for producing an notification without recommending further lab test is approximately 20-40%. The estimated GFR level or estimated CKD stages may be continuously or periodically (such as at specified time intervals or upon a triggering event) monitored to track the progression of the patient's renal function.

The above detailed description includes references to the accompanying drawings, which form a part of the detailed description. The drawings show, by way of illustration, specific embodiments in which the disclosure may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the disclosure should be determined with reference to the appended claims, along with the full scope of equivalents to which such claims are entitled.

What is claimed is:

1. A system for identifying a patient's risk of renal dysfunction, the system comprising:
   sensor circuits including sense amplifier circuits to sense at least first and second physiological signals, the first physiological signal including a heart sound signal, the second physiological signal including a cardiac or respiratory signal;
   a signal processor circuit configured to generate a first signal metric from the sensed heart sound signal and a second signal metric from the second physiological signal;
   a risk stratifier circuit coupled to the signal processor circuit, the risk stratifier circuit configured to:
      generate a primary renal risk indication using at least the first signal metric, and
      generate a secondary renal risk indication using at least the second signal metric; and
      generate a composite cardiorespiratory index indicative of prediction of a future renal dysfunction using a combination of the primary and secondary renal risk indications;
   a cardiac event detector circuit configured to detect a worsening heart failure (WHF) event;
   a controller circuit configured to determine an operating mode of the cardiac event detector circuit according to the composite cardiorespiratory index, and to control the cardiac event detector circuit to detect the WHF event in accordance with the determined operating mode, and
   wherein to determine the operating mode of the cardiac event detector circuit includes to use a first detection algorithm if the composite cardiorespiratory index exceeds a threshold, and to use a second detection algorithm if the composite cardiorespiratory index is below the threshold, the first detection algorithm having a higher sensitivity or a lower specificity than the second detection algorithm.

2. The system of claim 1, wherein, to generate the primary renal risk indication, the risk stratifier circuit is configured to generate a chronic kidney disease (CKD) indication using at least the first signal metric,
wherein, to generate the secondary renal risk indication, the risk stratifier circuit is configured to generate a secondary CKD indication using at least the second signal metric,
wherein, to generate the composite cardiorespiratory index, the risk stratifier circuit is configured to generate a composite CKD indication indicative of the prediction of the future renal dysfunction using a combination of the primary and secondary CKD indications.

3. The system of claim 2, wherein the risk stratifier circuit is further configured to generate an estimated glomerular filtration rate (eGFR) based on the composite CKD indication.

4. The system of claim 1, comprising an output circuit configured to present the composite cardiorespiratory index to a user or a process, and to generate an alert in response to the composite cardiorespiratory index satisfying a specific condition.

5. The system of claim 2, wherein the cardiac event detector circuit is configured to detect the WHF event using the composite CKD indication.

6. The system of claim 1, wherein the first signal metric includes one of:
an intensity measure of a first heart sound (S1), a second heart sound (S2), a third heart sound (S3), or a fourth heart sound (S4);
a ratio of a S3 intensity to a reference heart sound intensity, the reference heart sound intensity including one of a S1 intensity, a S2 intensity, or a heart sound energy during a specified portion of a cardiac cycle; or
a pre-ejection period, including a time interval between a Q wave and a S1 heart sound within a cardiac cycle.

7. The system of claim 2, wherein:
the sense amplifier circuits are further configured to sense a third physiological signal;
the signal processor circuit is configured to generate a third signal metric from the third physiological signal; and
the risk stratifier circuit is configured to generate the secondary CKD indication using at least the second and the third signal metrics.

8. The system of claim 7, wherein the risk stratifier circuit is configured to generate the secondary CKD indication using a plurality of measurements of the second signal metric when the third signal metric satisfies a specified condition.

9. The system of claim 7, wherein the third physiological signal includes a physical activity signal, and the third signal metric includes one of:
a physical activity level; or
a time duration when the physical activity level meets a specified condition.

10. The system of claim 2, wherein the risk stratifier circuit is configured to adjust the composite CKD indication using clinical information about the patient, the clinical information including one or more of:
a historical renal decompensation event;
one or more comorbidities of CKD;
a creatinine blood test;
patient physical assessment; or
patient demographics.

11. A method for identifying a patient's risk of renal dysfunction using a medical system, the method comprising:
sensing, via the medical system, at least first and second physiological signals, the first physiological signal including a heart sound signal, the second physiological signal including a cardiac or respiratory signal;
processing, via the medical system, the sensed heart sound signal to generate a first signal metric and processing the second physiological signal to generate a second signal metric;
estimating a risk of renal dysfunction via the medical system, including:
generating a primary renal risk indication using at least the first signal metric and generating a secondary renal risk indication using at least the second signal metric; and generating a composite cardiorespiratory index indicative of a prediction of a future renal dysfunction using a combination of the primary and secondary renal risk indications;
determining an operating mode of a cardiac event detector circuit according to the composite cardiorespiratory index;
detecting a worsening heart failure (WHF) event using the cardiac event detector circuit in accordance with the determined operating mode; and
wherein to determine the operating mode of the cardiac event detector circuit includes to use a first detection algorithm if the composite cardiorespiratory index exceeds a threshold, and to use a second detection algorithm if the composite cardiorespiratory index is below the threshold, the first detection algorithm having a higher sensitivity or a lower specificity than the second detection algorithm.

12. The method of claim 11, wherein generating the primary renal risk indication includes generating a primary chronic kidney disease (CKD) indication,
wherein generating the secondary renal risk indication includes generating a secondary CKD indication,
wherein generating the composite cardiorespiratory index includes generating a composite CKD indication indicative of the prediction of the future renal dysfunction using a combination of the primary and secondary CKD indications.

13. The method of claim 12, comprising:
generating an estimated glomerular filtration rate (eGFR) based on the composite CKD indication; and
generating an alert in response to the composite CKD indication or the eGFR satisfying a specific condition.

14. The method of claim 12, further comprising adjusting the operating mode of the cardiac event detector based at least on the composite CKD indication, and detecting the WHF event using the cardiac event detector in accordance with the adjusted operating mode.

15. The method of claim 12, further comprising sensing a third physiological signals and processing the third physiological signal to generate a third signal metric,
wherein the secondary CKD indication is generated using at least the second and the third signal metrics, and
wherein the third signal metric is generated from a physical activity signal.

16. The method of claim 15, wherein generating the secondary CKD indication includes sampling a plurality of measurements of the second signal metric when the third signal metric satisfies a specified condition, and generating the secondary CKD indication using the sampled measurements of the second signal metric.

17. The method of claim 12, comprising adjusting the composite CKD indication based on clinical information about the patient, the clinical information including one or more of:
- a historical renal decompensation event;
- one or more comorbidities of CKD;
- a creatinine blood test;
- patient physical assessment; or
- patient demographics.

18. A system for identifying a patient's risk of renal dysfunction, the system comprising:
- sensor circuits including sense amplifier circuits to sense at least a first cardiac or respiratory signal and a second cardiac or respiratory signal different from the first cardiac or respiratory signal;
- a signal processor circuit configured to generate a first signal metric from the first cardiac or respiratory signal and a second signal metric from the second cardiac or respiratory signal;
- a risk stratifier circuit coupled to the signal processor circuit, the risk stratifier circuit configured to:
  generate a primary renal risk indication using at least the first signal metric, and generate a secondary renal risk indication using at least the second signal metric;
  generate a composite cardiorespiratory index indicative of a prediction of a future renal dysfunction using a combination of the primary and secondary renal risk indications; and
  categorize the composite cardiorespiratory index into one of a plurality of risk degrees;
- a cardiac event detector circuit configured to detect a worsening heart failure (WHF) event;
- a controller circuit configured to determine an operating mode of the cardiac event detector circuit according to the categorized composite cardiorespiratory index, and to control the cardiac event detector circuit to detect the WHF event in accordance with the determined operating mode; and
- wherein to determine the operating mode of the cardiac event detector circuit includes to use a first detection algorithm if the composite cardiorespiratory index exceeds a threshold, and to use a second detection algorithm if the composite cardiorespiratory index is below the threshold, the first detection algorithm having a higher sensitivity or a lower specificity than the second detection algorithm.

19. The system of claim 18, wherein at least one of the first cardiac or respiratory signal, or the second cardiac or respiratory signal, is a heart sound signal.

* * * * *